United States Patent
Kölby-Falk

(10) Patent No.: US 6,554,813 B2
(45) Date of Patent: Apr. 29, 2003

(54) ABSORBENT INTRALABIAL SANITARY PROTECTION DEVICE

(75) Inventor: Ewa Kölby-Falk, Göteborg (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/992,016

(22) Filed: Nov. 26, 2001

(65) Prior Publication Data
US 2002/0065501 A1 May 30, 2002

Related U.S. Application Data
(60) Provisional application No. 60/252,594, filed on Nov. 24, 2000.

(51) Int. Cl.⁷ ............................................. A61F 13/15
(52) U.S. Cl. ..................... 604/385.17; 604/385.18; 604/385.03; 604/364; 604/368; 604/387
(58) Field of Search ................ 604/364, 367, 604/368, 386, 387, 385.03, 385.17, 385.18

(56) References Cited

U.S. PATENT DOCUMENTS

| | | | |
|---|---|---|---|
| 5,061,259 A | | 10/1991 | Goldman et al. |
| 5,683,373 A | * | 11/1997 | Darby .................... 604/385.01 |
| 5,731,365 A | | 3/1998 | Engelhardt et al. |
| 5,928,452 A | * | 7/1999 | McFall et al. .............. 156/269 |
| 5,947,945 A | * | 9/1999 | Cree et al. ................... 604/368 |
| 5,968,026 A | * | 10/1999 | Osborn et al. ............... 604/378 |
| 6,131,736 A | * | 10/2000 | Farris et al. ................. 206/440 |
| 6,171,292 B1 | * | 1/2001 | Osborn et al. .......... 604/385.17 |
| 6,409,713 B1 | * | 6/2002 | Osborn et al. .......... 604/385.17 |
| 6,416,501 B2 | * | 7/2002 | Brown et al. ........... 604/385.17 |
| 6,432,096 B1 | * | 8/2002 | McFall et al. .......... 604/385.17 |
| 6,461,340 B1 | * | 10/2002 | Lenker et al. .......... 604/385.17 |

FOREIGN PATENT DOCUMENTS

| | | |
|---|---|---|
| EP | 1 099 447 | 5/2001 |
| WO | WO 00/02509 | 1/2000 |
| WO | WO 00/40197 | 7/2000 |

* cited by examiner

Primary Examiner—Weilun Lo
Assistant Examiner—Michael G. Bogart
(74) Attorney, Agent, or Firm—Burns, Doane, Swecker & Mathis, LLP

(57) ABSTRACT

An absorbent sanitary protection device, designed so as to be worn intralabially, includes an absorption body with a first surface which is intended to face a wearer during use and a second surface which is intended to face away from the wearer during use. The absorption body of the sanitary protection device is made from a preformed, dehydrated hydrogel and is in the shape of a spoon with a cup-shaped portion arranged on the first surface and an elongate handle-shaped portion which, by way of the preforming, includes a portion which, on wetting, swells and forms a raised portion on the first surface of the protection device.

20 Claims, 2 Drawing Sheets

ABSORBENT INTRALABIAL SANITARY PROTECTION DEVICE

PRIORITY INFORMATION

Figure 1:
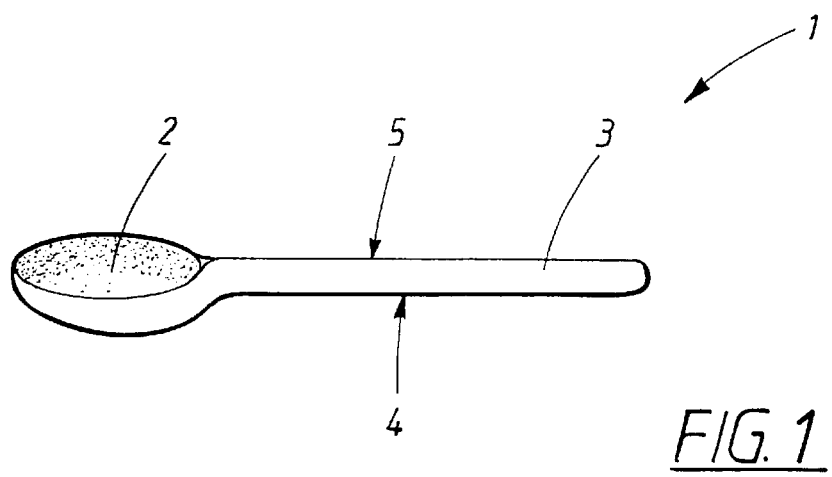

This application claims priority under 35 U.S.C. §§ 119 and/or 365 to U.S. Provisional Application No. 60/252,594 filed on Nov. 24. 2000; the entire content of which is hereby incorporated by reference.

FIELD OF THE INVENTION

The invention relates to an absorbent sanitary protection device which is designed so as to be worn intralabially and comprises an anatomically shaped absorption body with a first surface which is intended to face a wearer during use and a second surface which is intended to face away from the wearer during use.

DESCRIPTION OF THE RELATED ART

There are a great many different types of absorbent protection devices for use in connection with menstruation. The most common are sanitary napkins and panty liners which are absorbent protection devices which are worn outside the body and are in most cases fastened in the briefs of the wearer and therein collect and absorb the menstrual fluid discharged. Internal sanitary protection devices also exist in the form of tampons, or liquid-collecting arrangements which are inserted into the vagina of the user. A third category of sanitary protection devices, which have thus far not achieved market penetration, are what are known as intralabial protection devices, which are worn entirely or partly between the labia of the wearer. Such protection devices combine the advantages of both the other types of sanitary protection devices. The intralabial protection devices are therefore small and unobtrusive to wear, like the internal protection devices. Furthermore, the intralabial protection devices are not inserted into the vagina, which many wearers consider an advantage.

However, previously known intralabial protection devices suffer from a number of disadvantages, which has resulted in them not achieving commercial success in spite of their good characteristics. One problem is to keep the protection device in place during use. If the protection device is fastened in a conventional manner by way of adhesive or the like in the briefs of the wearer, it will move together with the briefs when the wearer moves. There is a risk of it moving out of position and losing its contact with the body of the wearer. As an intralabial protection device must be made relatively small and short so as to be accommodated between the labia of the wearer, even small movements of the protection device results in the risk of leakage past the protection device being drastically increased. If, however, the protection device is not fastened in the use position at all, there is a risk that it will fall out or move if a gap arises between the body of the wearer and the underwear. It is also a disadvantage if, when visiting the lavatory, the protection device comes loose and, for example, falls down into the toilet.

Another major problem is that the intralabial protection devices which have previously been available feel uncomfortable to wear. This is due to the fact that the region between the labia is very sensitive to chafing and pressure, and it has therefore proved to be virtually impossible to combine demands for a comfortable protection device with requirements for adequate absorption capacity and leakage security.

A demand therefore still exists for an effectively functioning intralabial sanitary protection device which is comfortable to wear and stays safely in place during use and which moreover affords satisfactory leakproofness.

By the present invention, however, an absorbent sanitary protection device of the type referred to in the introduction has been produced, in which the disadvantages and problems from which previously known sanitary protection devices for intralabial use suffered have been minimized. A product made according to one embodiment of the invention includes an absorption body which is made from a preformed, at least partly dehydrated hydrogel and is in the shape of a spoon with a cupshaped portion arranged on the first surface and an elongate handle-shaped portion which, by way of the preforming, comprises a portion which, upon wetting, swells and forms a raised portion on the first surface of the protection device.

As a result of the special design of the sanitary protection device, a particularly good anatomical fit and consequently good retention of the protection device during use as well as a high degree of leakage security are achieved. Moreover, it is ensured that the sanitary protection device is from the outset positioned correctly in relation to the body of the wearer. In this connection, the sanitary protection device is arranged with the spoon-shaped part over the clitoris of the wearer and the elongate handle part over the vaginal orifice. The accuracy of positioning which can in this way be brought about ensures that the raised portion will be formed in the correct place in relation to the body of the wearer.

Since an absorbent sanitary protection device according to the invention is relatively small and in this respect preferably has a length which does not exceed approximately 8.5 cm, it can be an advantage if the sanitary protection device comprises a gripping device for removal of the protection device after use. In this connection, suitable gripping devices are gripping loops, removal strings, gripping tabs or the like. The gripping device can be made of the same material as the remainder of the sanitary protection device and therefore constitute an integral part thereof, or the gripping device can alternatively be a separate component which is fastened to the sanitary protection device. In this connection, the gripping device can be molded into the hydrogel, or be glued, welded or mechanically fixed to the sanitary protection device.

A gripping device in the form of a gripping tab or a gripping loop can also be used in order to facilitate application of the sanitary protection device over the clitoris and the vaginal orifice.

The hydrogel is made of a material which does not irritate the mucous membranes of the wearer and can in this respect comprise polymers based on vinyl alcohol, polyacrylate, polymethacrylate, polyethylene oxide, polysaccharide, acrylamide, vinyl pyrrolidone, polyethers, amino acids or urethane, and also mixtures, copolymers and derivatives thereof.

When the sanitary protection device is manufactured by molding in a mold, a skin-like surface is formed on the second surface of the hydrogel. Such a skin-like surface functions as a liquid barrier which prevents liquid from leaking out from the protection device. Alternatively, it is of course possible to provide the sanitary protection device with a separate liquid-blocking layer in the form of a plastic film, or a coating of a liquid-blocking material.

The absorbent sanitary protection device is imparted, preferably by molding swollen hydrogel, an anatomically adapted shape with a cup-shaped front portion and an elongate rear portion with a raised portion. The shaped swollen hydrogel is dehydrated, entirely or at least to such an extent that the hydrogel can reabsorb liquid when it is subjected to wetting during use in an absorbent sanitary protection device. The resulting protection device is, after dehydration, ready for use.

When the protection device is used, the hydrogel will absorb bodily fluid and then swell to its original, predetermined shape with a rear raised portion. At the same time, the surface of the hydrogel becomes sticky, which, in a gentle and comfortable manner, allows easy adhesion of the protection device to the mucous membranes between the labia of the wearer. During the course of absorption, an underpressure also arises in the absorption material, which contributes to the protection device being retained against the body of the wearer. The sticky surface remains moist during use, which results in the risk of the mucous membranes of the wearer drying out being eliminated. When use is made of conventional fibrous absorption materials and conventional surface materials which are designed so as to carry liquid away rapidly from the surface of the absorbent product, drying out of the mucous membranes is a considerable problem. Moreover, a dry surface on an absorbent product which is in contact with sensitive body surfaces, such as mucous membranes, leads to an increased risk of chafing and other mechanical irritation.

The adhesion capacity of the wet hydrogel, together with the anatomically adapted shape of the sanitary protection device, results in the protection device staying safely in place during use, without chafing or otherwise irritating the mucous membranes of the wearer. The exceptionally good fit and reliable attachment makes it possible to design the protection device so as to be small and unobtrusive, without jeopardizing the leakage security. This means that the protection device is less bulky and uncomfortable to wear than the previously known intralabial protection devices which consist essentially of conventional fibrous absorption materials.

If greater absorption capacity is required, or when the anticipated liquid flow is relatively great, the liquid absorption capacity of the sanitary protection device can be increased by arranging an absorption material with a higher liquid absorption rate inside the raised portion of the protection device. A suitable such absorption material is absorbent foam. The inner absorption material is preferably exposed for receiving liquid through an opening in the hydrogel on the first surface of the sanitary protection device.

According to an alternative embodiment, the sanitary protection device can be designed with a raised portion, in which one or more-cavities or wells are arranged, which are open for liquid to flow in on the first side of the sanitary protection device. Liquid which cannot be absorbed immediately by the hydrogel can be caught temporarily in the wells and then absorbed gradually by the hydrogel. This embodiment is a simpler variant of the embodiment mentioned previously with an inner absorption body in the raised portion.

The absorbent sanitary protection device according to the invention is preferably designed so as to follow the anatomy closely in the genital area of a female wearer. In this connection, the spoon-shaped portion preferably has a length of between 15–20 mm, and the handle part has a length of between 55–65 mm. If the sanitary protection device is provided with a raised portion, this should preferably be positioned at a distance from the spoon-shaped portion of approximately 10 mm, measured in the longitudinal direction of the protection device. The raised portion then preferably has a length of between 30–35 mm, which leaves an essentially plane portion behind the raised portion with an extent in the longitudinal direction which is between 15–20 mm. The overall length of the sanitary protection device is preferably approximately 85 mm. The width, that is to say the extent in the transverse direction, of the sanitary protection device is preferably between 5–20 mm, and more preferably between 10–15 mm, at the widest point of the spoon-shaped portion. The handle-shaped portion preferably has a maximum width of 20 mm, and the width of the raised portion is approximately 10 mm.

One advantage of a protection device according to the invention is that its small size and great flexibility allow the protection device to be flushed away after use. A used protection device can therefore be disposed of in a simple and convenient manner.

A sanitary protection device according to the invention can, in the event of heavy flows or when increased leakage security is desired, for example for night use, be used in combination with a panty liner or a sanitary towel.

BRIEF DESCRIPTION OF THE DRAWING FIGURES

Figure 2:
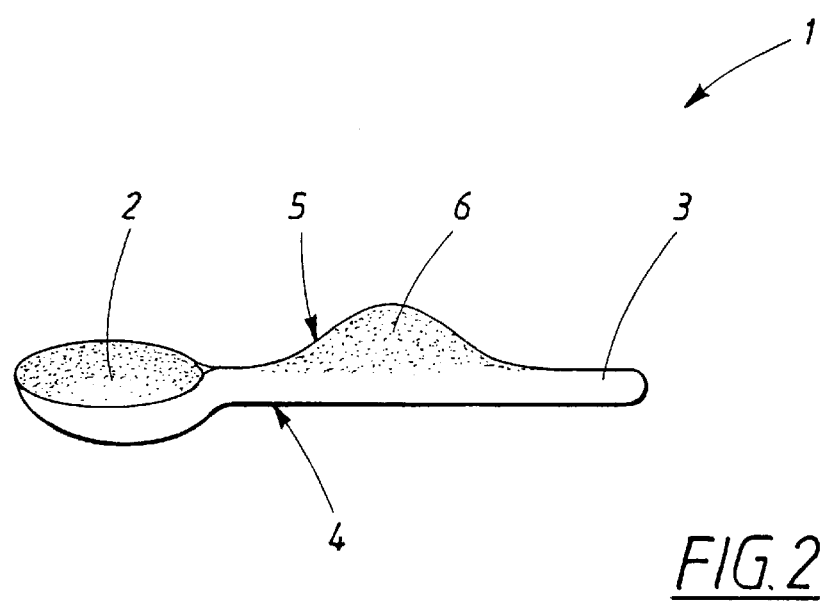
Figure 3:
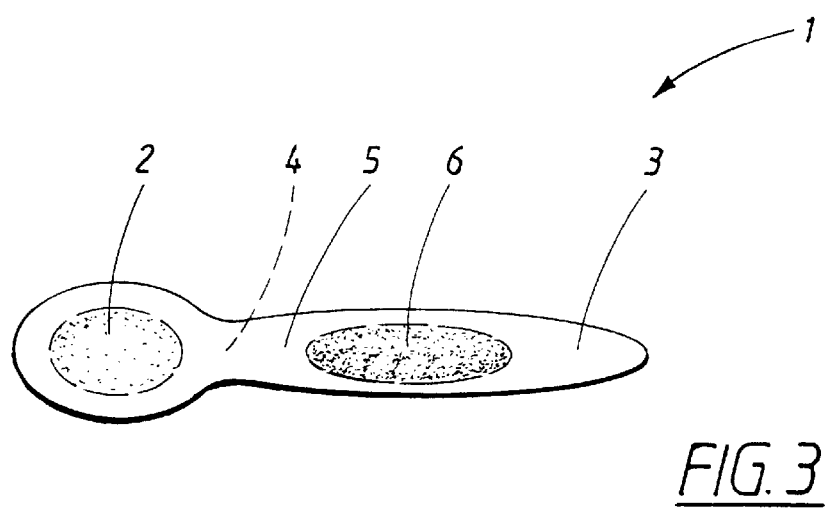
Figure 4:
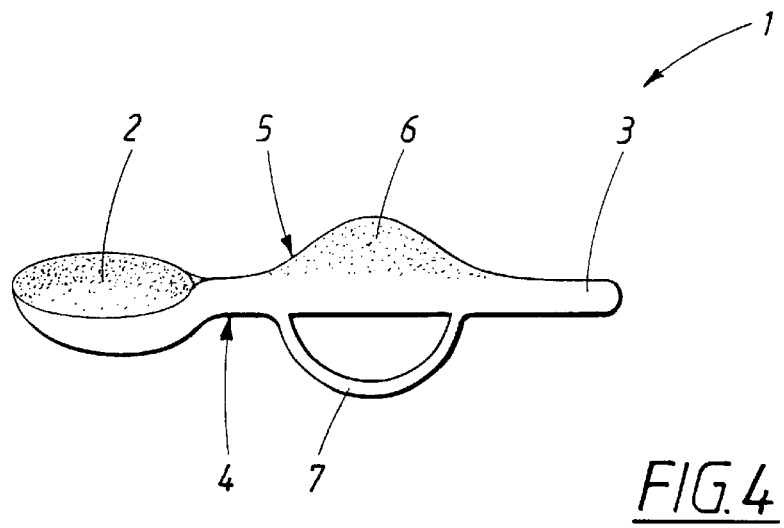
Figure 5:
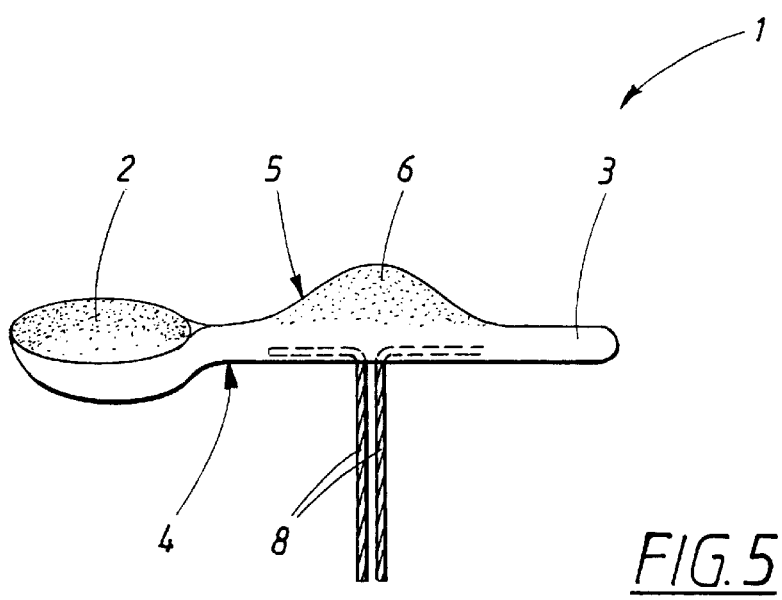
Figure 6:
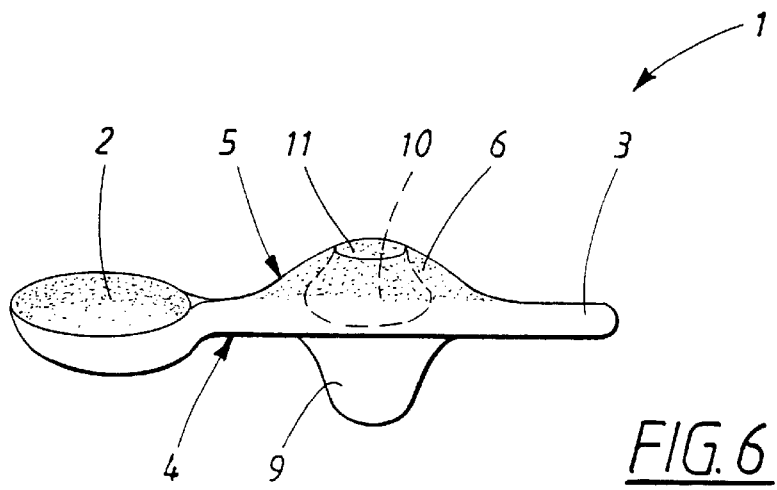

The invention will be described in greater detail below with reference to the exemplary embodiments shown in the appended drawings, in which FIG. 1 shows a side view of a sanitary protection device as it appears before use, FIG. 2 shows a side view of the sanitary protection device in FIG. 1 as it appears during use, after wetting, FIG. 3 shows the sanitary protection device in FIGS. 1 and 2, seen from above, in its state of use, FIG. 4 shows a side view of a sanitary protection device according to an embodiment of the invention, FIG. 5 shows a side view of a sanitary protection device according to another embodiment of the invention, and FIG. 6 shows a sanitary protection device according to a further embodiment of the invention.

DETAILED DESCRIPTION OF THE PREFERRED EMBODIMENTS

The sanitary protection device 1 shown in FIGS. 1, 2 and 3 is made from hydrogel which has been molded into the spoon shape shown, with a front, cup-shaped portion 2 which is intended to face forwards on the wearer during use and is arranged with the cup-shaped portion against the body of the wearer, over the clitoris of the wearer. The sanitary protection device also has an elongate rear portion 3 which is to face backwards on the wearer during use and be positioned over the vaginal orifice and extend backwards towards the perineum.

The sanitary protection device 1 has a lower surface 4 which is intended to face away from the wearer during use. In this connection, the lower surface is preferably liquid impermeable and can consist of a layer of liquid impermeable material, such as plastic film, or a coating of a liquid impermeable material. Alternatively, the sanitary protection device can be manufactured in such a manner that a liquid impermeable skin is formed on the lower surface.

The sanitary protection device 1 also has an upper surface 5 which is intended to face the wearer when the protection device is in use. The upper surface 5 receives liquid and admits it into the sanitary protection device. For this purpose, the upper surface can be covered by an open surface layer of hydrophilic or hydrophobic material. If the liquid-receiving surface consists of a hydrogel surface, a slightly sticky, adhesive and moist surface is obtained during absorption, which is advantageous because it is gentle to the mucous membranes of the wearer and it ensures that the sanitary protection device stays safely in place during use.

When the sanitary protection device is wetted during use, the hydrogel absorbs liquid and swells, whereupon the rear portion 3 forms a raised portion 6, as shown in FIGS. 2 and 3. The shape and size of the raised portion 6 are already determined during manufacture of the sanitary protection device when the swollen hydrogel is molded into an anatomically adapted shape. When the hydrogel swells, its surface also becomes moist and slightly sticky, which affords soft and comfortable adhesion of the protection device to the body of the wearer and keeps the mucous membranes between the labia of the wearer moist. This results in the risk of drying out and chafing of the mucous membranes being eliminated. The swollen hydrogel is soft and flexible, and also elastic, which means that the sanitary protection device according to the invention is virtually imperceptible for the wearer when it is being worn. By virtue of the soft structure of the protection device, the latter shapes itself according to the body of the wearer, and discomfort in the form of pressure or penetration of sharp corners or the like is avoided. The liquid underpressure which arises in the hydrogel during the course of absorption also contributes, as mentioned previously, to the adhesion capacity of the sanitary protection device and is therefore advantageous for retention of the protection device during use.

As a sanitary protection device according to the invention becomes soft, flexible and sticky after wetting, it is an advantage if it is provided with some form of gripping member which facilitates removal of the protection device after use. An example of such a gripping member in the form of a gripping loop 7 is shown in FIG. 4. The gripping loop 7 can be formed from hydrogel and can in this connection be molded together with the sanitary protection device 1 itself. Alternatively, the gripping loop 7 can be a separate component and include, for example, a string loop, a plastic band, a metal loop or the like, which is molded, glued or welded firmly on the sanitary protection device.

FIGS. 5 and 6 show further examples of gripping members. FIG. 5 shows a sanitary protection device 1, into which two gripping strings 8 have been molded. It is of course possible to use only one gripping string 8 and to fasten the string or the strings in another manner, such as by welding or gluing. It is also possible to envisage fastening a gripping string by tying it in the sanitary protection device. Such fastening is preferably carried out by providing the sanitary protection device with a through-hole (not shown) at the end of the elongate rear portion 3 and tying the gripping string through the hole.

FIG. 6 shows a gripping member in the form of a gripping tab 9. The gripping tab 9 can, in a manner corresponding to that indicated in connection with the gripping members described previously, be molded in one piece with the sanitary protection device 1, or be made from a separate material which is fastened to the sanitary protection device by molding, gluing or welding.

The sanitary protection device 1 shown in FIG. 6 differs from the protection device shown in FIGS. 1–5 as far as absorption is concerned in that the raised portion 6 comprises an absorption body 10 which is arranged inside the hydrogel and is made of a material with a higher absorption rate than the surrounding hydrogel. Such an embodiment is suitable when the sanitary protection device 1 is expected to receive heavier liquid flows and/or relatively great quantities of liquid. Materials which can be used for the inner absorption body 10 are fibrous material, absorbent foam, mixtures of fibrous material and superabsorbents or the like. A sanitary protection device according to the invention, with an inner absorption body 10, already has a small raised portion 6 in the elongate rear part 3 of the protection device before absorption. On wetting, however, the raised portion 6 swells further and assumes the predetermined shape and size shown in FIG. 6.

In order for it to be possible for liquid to be absorbed rapidly by the inner absorption body 10, the latter is exposed to liquid flow through an opening 11 in the hydrogel.

According to an embodiment which is not shown, the raised portion 6 of the sanitary protection device 1 can be provided with a well or cavity in the hydrogel, in which well or cavity liquid can be temporarily collected before it can be absorbed by the hydrogel. Such an embodiment is therefore similar to that shown in FIG. 6, but does not have the inner absorption body 10.

The different gripping members 7, 8, 9 shown are of course interchangeable, and the type of gripping member can therefore be selected freely, irrespective of the design of the remainder of the sanitary protection device 1.

The principles, preferred embodiments and manner of use of the present invention have been described in the foregoing specification. However, the invention which is intended to be protected is not to be construed as limited to the particular embodiments described. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the invention be embraced thereby.

What is claimed is:

1. An absorbent sanitary protection device, comprising:
   an absorption body with a first surface which is intended to face a body of a wearer during use and a second surface which is intended to face away from the body of the wearer during use, said absorption body being made from a preformed, at least partly dehydrated hydrogel;
   said absorption body further including a cup-shaped portion arranged on the first surface for positioning against the body of the wearer and an elongate handle-shaped portion arranged on the first surface which, by way of the preforming, comprises a portion which, on wetting, swells and forms a raised portion on the first surface.

2. The absorbent sanitary protection device according to claim 1, wherein the first surface has a sticky and adhesive surface after wetting.

3. The absorbent sanitary protection device according to claim 1, wherein the hydrogel comprising polymers based on vinyl alcohol, polyacrylate, polymethacrylate, polyethylene oxide, polysaccharide, acrylamide, vinyl pyrrolidone, polyethers, amino acids or urethane, and also mixtures, copolymers and derivatives thereof.

4. The absorbent sanitary protection device according to claim 1, further comprising a gripping device for removal of the protection device after use.

5. The absorbent sanitary protection device according to claim 4, wherein the gripping device is a gripping loop.

6. The absorbent sanitary protection device according to claim 4, wherein the gripping device is a gripping string.

7. The absorbent sanitary protection device according to claim 4, wherein the gripping device is a gripping tab.

8. The absorbent sanitary protection device according to claim 1, wherein the raised portion includes an inner cavity or well which is formed in the hydrogel.

9. The absorbent sanitary protection device according to claim 1, wherein the raised portion comprises an internal absorption body made of an absorption material with a higher absorption rate than the hydrogel.

10. The absorbent sanitary protection device according to claim 8, the internal absorption body is made of an absorbent foamed material.

11. The absorbent sanitary protection device according to claim 1, wherein the length of the sanitary protection device not exceeding 8.5 cm.

12. An absorbent sanitary protection device, comprising:
    means for absorbing fluids from a body of a wearer, said absorption means including a first surface which is intended to face the body of the wearer during use and a second surface which is intended to face away from the body of the wearer during use, said absorption means being made from a preformed, at least partly dehydrated hydrogel;
    front positioning means for positioning the device against a front portion of the body of the wearer, said front positioning means being arranged on the first surface; and
    rear positioning means for positioning the device against a rear portion of the body of the wearer, said rear positioning means being arranged on the first surface and including expansion means, which, on wetting, swells and forms a raised portion on the first surface.

13. The absorbent sanitary protection device according to claim 12, wherein the first surface has a sticky and adhesive surface after wetting.

14. The absorbent sanitary protection device according to claim 12, wherein the hydrogel comprising polymers based on vinyl alcohol, polyacrylate, polymethacrylate, polyethylene oxide, polysaccharide, acrylamide, vinyl pyrrolidone, polyethers, amino acids or urethane, and also mixtures, copolymers and derivatives thereof.

15. The absorbent sanitary protection device according to claim 12, wherein the raised portion includes an inner cavity or well which is formed in the hydrogel.

16. The absorbent sanitary protection device according to claim 12, wherein the raised portion comprises an internal absorption body made of an absorption material with a higher absorption rate than the hydrogel.

17. The absorbent sanitary protection device according to claim 12, the internal absorption body is made of an absorbent foamed material.

18. The absorbent sanitary protection device according to claim 12, wherein the length of the sanitary protection device not exceeding 8.5 cm.

19. The absorbent sanitary protection device according to claim 1, further comprising a gripping device for removal of the protection device after use.

20. A method of using an absorbent sanitary protection device, comprising the steps of:
    providing an absorbent sanitary protection device having an absorption body formed into a spoon shape from swollen hydrogel; and
    positioning the absorbent sanitary protection device onto a body of a user whereby upon wetting, the absorption body swells and forms a raised portion on the absorption body.

* * * * *